United States Patent

Glass et al.

Patent Number: 6,008,057
Date of Patent: Dec. 28, 1999

[54] IMMUNOASSAY SYSTEM

[75] Inventors: Thomas R. Glass, Idaho City, Id.; Myron J. Block, North Salem, N.H.

[73] Assignee: Roche Diagnostics Corporation, Indianapolis, Ind.

[21] Appl. No.: 08/406,380

[22] Filed: Mar. 17, 1995

Related U.S. Application Data

[63] Continuation-in-part of application No. 07/939,419, Sep. 3, 1992, abandoned, which is a continuation of application No. 07/398,717, Aug. 25, 1989, abandoned.

[51] Int. Cl.⁶ .................. G01N 33/557; G01N 33/543; G01N 33/53

[52] U.S. Cl. .................. 436/517; 436/518; 436/527; 436/531; 436/800; 436/805; 435/4; 435/7.1; 435/7.93; 435/7.94; 435/973

[58] Field of Search .................. 436/517, 518, 436/527, 531, 800, 805; 435/7.1, 7.94, 7.93, 973

[56] References Cited

U.S. PATENT DOCUMENTS

| | | | |
|---|---|---|---|
| 3,652,761 | 3/1972 | Weetall | 424/12 |
| 4,166,105 | 8/1979 | Hirschfield | 424/3 |
| 4,376,110 | 3/1983 | David et al. | 436/513 |
| 4,385,126 | 5/1983 | Chen et al. | 436/518 |
| 4,558,014 | 12/1985 | Hirschfield et al. | 436/527 |
| 4,582,809 | 4/1986 | Block et al. | 436/527 |
| 4,618,485 | 10/1986 | Tsay et al. | 424/1.1 |
| 4,808,521 | 2/1989 | Allen | 435/7 |
| 4,849,338 | 7/1989 | Litman et al. | 435/7 |
| 4,923,819 | 5/1990 | Fernandez et al. | 436/518 |
| 5,171,695 | 12/1992 | Ekins | 436/501 |

FOREIGN PATENT DOCUMENTS

| | | |
|---|---|---|
| WO 80/02076 | 10/1980 | WIPO . |
| WO 88/01058 | 2/1988 | WIPO . |
| WO 89/09408 | 10/1989 | WIPO . |

OTHER PUBLICATIONS

Yuan A. S. Rudio F. M. and S.E. Wagner (1988) "A Dual Radioimmunoassay for the Detection of Morphine and Cocaine in Urine" *Clinical Chemistry* 34(6):1161 Abstract 040.

Burdon R. H. and P.H. van Knippenberg (1985) "The Immobilization of Immunoreactants on Solid Phases" in *Practice and Theory of Emzyme Immunoassays* Tijssen, P. (Amsterdam, Elsevier) 297–8.

Burdon R. H. and P.H. van Knippenberg (1985) "Quantitative Enzyme Immunoassay Techniques" in *Practice and Theory Of Emzyme Immunoassays* by Tijssen, P. (Amsterdam, Elsevier) 329,332,376–377.

Smith, T. W. and Skubitz, K. M. (1975) "Kinetics of Interactions Between Antibodies and Haptens" *Biochemistry* 14(7):1496–1502.

*Primary Examiner*—Keith D. MacMillan
*Assistant Examiner*—P. Ponnaluri
*Attorney, Agent, or Firm*—Lahive & Cockfield, LLP

[57] ABSTRACT

Disclosed is a method of assaying, in assay apparatus, for at least the ligand intended to be used to assay analyte in a sample, with which analyte the ligand will specifically bind. The method provides a product in which a ligand is labeled with a detectable tag and is immobilized on an appropriate substrate. An assay is made to measure the immobilized, labeled ligand by detecting the tag labeling the latter. The product can then be used to assay for the analyte by contacting the latter so as to form a complex. The extent and rate of specific binding of the analyte in the complex is identifiable, either by competition assay or sandwich assay as a rate of change, so the relative proportions of analyte and ligand are readily determinable.

11 Claims, 1 Drawing Sheet

IMMUNOASSAY SYSTEM

REFERENCE TO RELATED APPLICATIONS

The present application is a continuation-in-part of U.S. patent application Ser. No. 07/939,419, filed Sep. 3, 1992, now abandoned, which is a continuation of U.S. patent application Ser. No. 07/398,717, filed Aug. 25, 1989, now abandoned the disclosures of which are incorporated herein by reference.

BACKGROUND OF THE INVENTION

This invention relates to chemical and biochemical assays involving one or more ligands that will specifically bind to respective reactive moieties of interest.

A number of known chemical or biochemical analyte/ligand reactions in which a complex is formed by the reaction of moieties that will highly specifically bind to one another, are used as the basis for biochemical or chemical assays. Particularly, the well known immune reaction involving the formation of antibody-antigen complexes, nucleic acid hybridizations, enzyme-inhibitor, enzyme-coenzyme, hormone-receptor, enzyme-receptor and like substrate-specific reactions are exemplary of some of those known specific binding reactions. The terms "moiety" and "ligand" as used herein generally interchangeably refer to the reactive portions of such complex; with respect to an antigen-antibody complex, for example, these terms are intended to include all immunologically reactive portions such as haptens, complete antigens, reactive antigen-antibody fragments, and complete antibodies. The term "analyte" is intended to refer to the moiety or ligand being assayed either qualitatively, quantitatively or both, and the term "captor" is intended to refer to the ligand or moiety that will specifically bind to the analyte of interest.

Assays based upon these well known specific binding reactions involve a wide variety of techniques. Some assay methods employ radioactive, luminescent or fluorescent tags that are coupled to either the ligand or to the analyte. Those tags can be detected or measured from the radiation arising from the reaction product or complex. For example, a fluorescence assay system using an attenuated total reflection (ATR) cell is shown and described in detail in U.S. Pat. No. 4,558,014 issued Dec. 10, 1985 and is incorporated herein by reference.

Where such a typical assay cell is a disposable unit used for a single sample assay, in a number of instances the captor ligands may not be covalently bonded to the substrate, but may simply be adsorbed thereon for convenience, cost or other reasons. Contacting the cell with the sample containing the analyte, however, may wash off some of the adsorbed captors, reducing the signal so that it becomes difficult to correlate signal strength with concentration from sample to sample.

Further, stringent quality control measures are usually required in order to manufacture single-assay, disposable, coated cells that respond substantially identically. In practice, one samples a large population of such cells, and then checks the cells with a standardized assay to see if the sampled cells respond within a desired tolerance. It also may not be either necessary or desirable to manufacture cells that are disposable after each use, and in such case consideration should be given to sequential use of a cell to assay several different samples.

Accordingly, a principal object of the present invention is to provide a method of readily and easily determining the amount or concentration of the immobilized ligand on the substrate for use in a capture assay. Another object of the present invention is to provide an assay method that will permit the determination of both the concentration of the immobilized ligand as well as providing a measurement of the analyte in a sample, which analyte will specifically bind with such ligand.

Other objects of the present invention will in part be obvious and will in part appear hereinafter.

SUMMARY OF THE INVENTION

The invention accordingly comprises the method comprising the several steps and the relation of one or more of such steps with respect to each of the others, and the product possessing the features, properties and relation of components, all of which are exemplified in the following detailed disclosure, and the scope of the application of which will be indicated in the claims.

For a fuller understanding of the nature and objects of the present invention, reference should be made to the following detailed description taken in connection with the accompanying drawing wherein there is shown an idealized, partly fragmentary, partly cross-sectional view of apparatus for carrying out the method of the present invention.

To effect the foregoing objects, the product of the present invention comprises a substrate on which a species of captor ligand is immobilized, the species being labeled with a type of tag that will, under given circumstances, provide a signal proportional to the concentration or number of labeled ligands on the substrate.

Thus, in the method of the present invention, a substrate is coated with a tagged immobilized ligand to establish a reaction surface on which an analyte of interest in the sample to be assayed will specifically bind to the ligand to form a complex. Specific binding is effected by contacting the sample with the immobilized ligand which has been preferably pretagged with a first label that, for example, when properly excited, fluoresces to provide a first distinguishable signal at a first wavelength $w_1$. In a competition type of assay using the method and product of the present invention, a known quantity of the analyte of interest with which the captor ligand will react by specific binding, is tagged with a second label that, when appropriately excited, thereby provides a second signal distinguishable from the first signal. Distinguishing the second signal from the first may be accomplished either by using a second label that will fluoresce at a second wavelength $w_2$, or by temporal separation using the same label for both the captor ligand and the known quantity of analyte. In temporal separation, fluorescence from the ligand bound to the solid phase will be measured first in the absence of analyte. The second signal from the tagged analyte is then measured as a rate of change in the total fluorescent signal. Similarly, rate of change measurements can be utilized with different labels, with the rate of change in the amount of the second label showing the kinetics of the reaction.

The known quantity of tagged analyte is mixed with a sample containing an unknown quantity of the untagged analyte and the two are contacted with the reaction surface of the product of the present invention. Measurement in one channel of the signal at $w_1$ will indicate how much captor is bound to the substrate. Measurement in a second channel of the signal at $w_2$ after combining the mixture of test body and tagged analyte and captor to form a complex, and subsequent washing if desired to remove unbound second label molecules, will indicate the extent of the untagged analyte from the sample that has become bound into the immobilized complex.

In a sandwich type of assay using the method and product of the present invention, the analyte in the test body is allowed to complex and after becoming specifically bound to the immobilized captor ligand, is contacted with a reagent comprising free ligand that will further complex with the immobilized analyte, the free ligand (preferably the same species of ligand as is immobilized on the substrate or reaction surface), being labeled with the second tag.

In either case, to obtain a determination of the ratio of bound analyte to immobilized ligand, measurement of the signals from both types of tags can advantageously be made and evaluated in real time, typically contemporaneously, i.e., either substantially simultaneously or in a sequence of observations or measurements taken within a comparatively short time with respect to the same sample under assay. Most preferably, rate of change measurements are used. It is preferred in most instances to make the observations as nearly simultaneously as possible to reduce any effects of fast changes in background.

It will be apparent that the assays using the product and method of the present invention are basically multiplex systems when used to measure both the immobilized ligand and the bound analyte, and are thus readily distinguishable from known multichannel assays in which two or more analytes are substantially simultaneously assayed using different labeled ligands that will respectively uniquely specifically bind to the corresponding analytes. Cf. A Dual Radioimmunoassay for the Detection of Morphine and Cocaine in Urine, A. S. Young, F. Rubio and S. E. Wagner, *Clinical Chemistry*, Vol. 34, No. 6, 1998, p. 1161.

BRIEF DESCRIPTION OF THE DRAWING

The sole FIGURE of the drawing illustrates an apparatus useful in carrying out the methods of the invention.

DETAILED DESCRIPTION OF THE INVENTION

Figure 1:
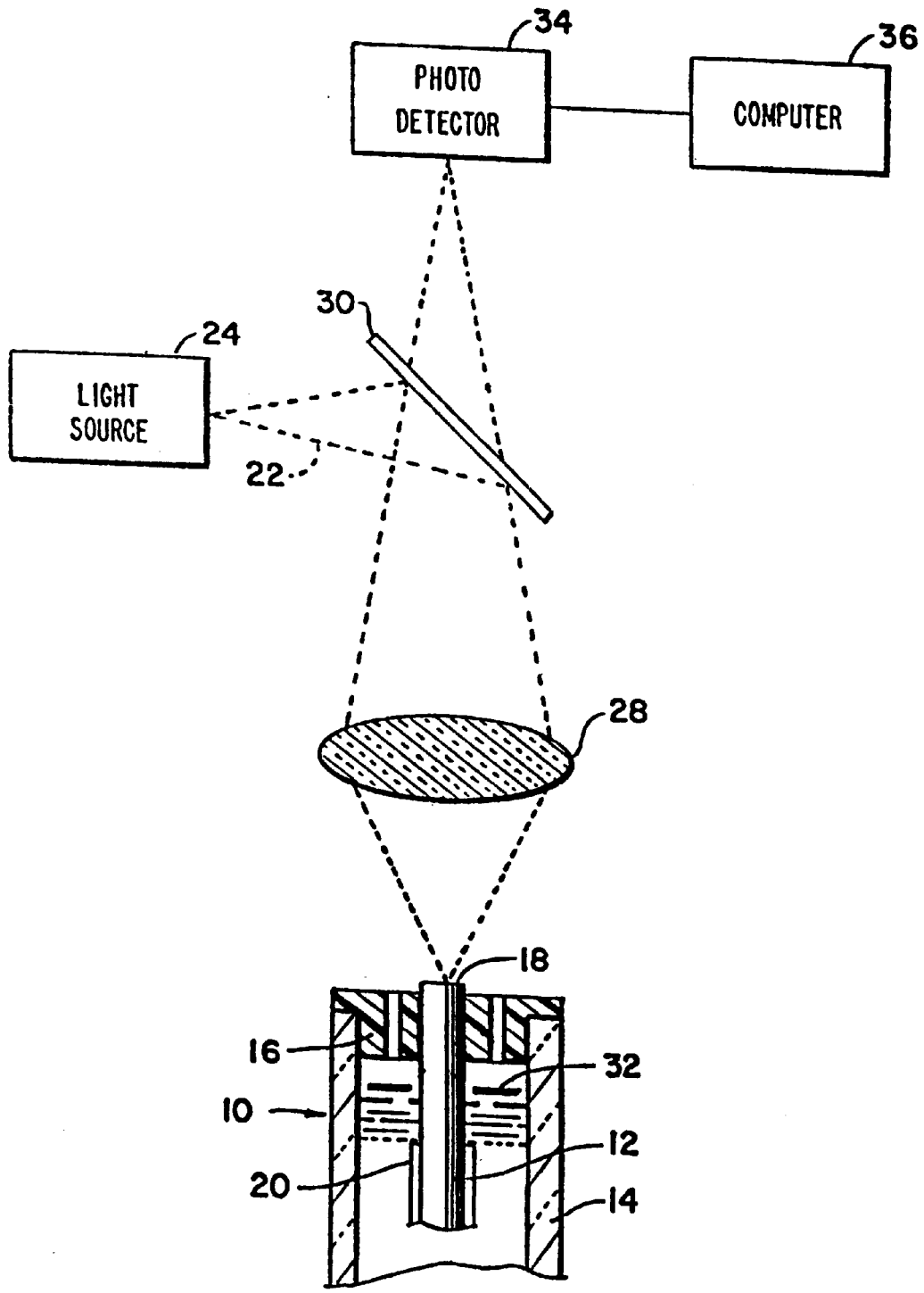

The present invention can advantageously be described in a context of a fluorescent immunoassay system employing fluorescent tags, particularly an assay employing one or more ATR cells, but it is to be understood that the principles of the invention extend to other types of assays involving specific binding reactions and employing other types of detectable tags. A distinct advantage is obtained by using such an ATR cell in the present invention, because fluorescent signals detected by such a cell arise only within the extremely shallow evanescent zone adjacent the reaction surface of the cell. Thus, the cell, per se, automatically segregates free ligands in the bulk sample outside the evanescent zone from those ligands that are bound to the reaction surface. Such ATR cells typically employ a cylindrical rod or fiber as the cell body, the reaction surface of such fiber being an activated zone where the captor ligand is immobilized at least on a portion of the substrate provided by the fiber surface.

In sandwich type assays, the amount of ligand immobilized on the reaction surface should be well in excess of the expected maximum amount of the analyte being assayed, thereby avoiding the possibility that the immobilized captor population will be saturated, cutting off accurate determination of the true maximum of the analyte concentration. The immobilized ligand, of course, can be an antibody where the analyte being assayed is an antigen, or the immobilized ligand can be the antigen where the ligand sought is an antibody.

Referring to the drawing, there is shown a cross-section of a fragment of totally internally reflecting assay cell 10. One preferred embodiment of cell 10 comprises a cylindrical rod or fiber 12 that is an elongated, substantially cylindrical, optically transparent body adapted to propagate along its length by multiple total internal reflections, optical radiation entering an end of the fiber within an established solid angle substantially rotationally symmetric about the longitudinal axis of the fiber. By way of example, fiber 12 may be any of a number of optically transparent materials such as glass, quartz, sapphire, polypropylene, polyolefins, nylon and the like, having an index of refraction greater than that of the fluid sample being assayed. As will be described hereinafter, a synthetic polymer is preferred inasmuch as the attachment thereto of some coatings can be effected more readily than to an inorganic substrate such as glass. Preferably, fiber 12 is enclosed within capillary tube 14 formed of a material that is relatively insoluble and non-reactive with the fluid being assayed. Fiber 12 passes through and is supported coaxially within capillary tube 14 typically by stopper 16, thereby disposing all of the fiber except for end face 18 within tube 14.

Disposed on a portion of the outer surface of fiber 12 is an immobilized or prebound coating 20 which, for example, can be formed of one of the reactants of an immune type reaction, i.e., a moiety of an antigen-antibody complex. Typically, coating may be applied by first providing the fiber surface or substrate with a plurality of coupling sites and then a number of the desired moieties of an antibody-antigen complex may be bound to those sites, typically but not necessarily covalently and in known manner. The coupling sites on the substrate to which the selected moieties of the antigen-antibody complex are initially immobilized are selected so as to provide the requisite immobilization without appreciably affecting the affinity and avidity of the moiety for the complementary portion of the complex. Where fiber 12 is glass, appropriate attachment sites may be provided as is well known, for example, by reacting a silyl compound with the glass surface. Coupling of other suitable silyl compounds, and methods by which carboxyl, amino and other reactive groups of antibody or antigen may be covalently bound to various inorganic materials are described by Weetall in U.S. Pat. No. 3,652,761. Binding of some species of analytes to polymers may be easier and there is a substantial body of literature describing the immobilization of antibodies and antigens on the surface of polymers.

Coating 20 may also be applied by adsorption in some instances, by simply wetting the cell surface with a suitable reagent having an appropriately selected moiety. Where the analyte is, for example, a protein, the latter will adsorb strongly on most types of glass. When using either glass or polymer substrates, it may be desirable to first coat the latter with protein A or the like to provide a mechanism for binding antibodies. Such precoating improves the probability that the coupling site of the antibody for the antigen will not be sterically hindered.

For example, the selected moiety to be immobilized on the ATR substrate would be a ligand of specified type that will bind specifically to the analyte of interest. Such ligand is tagged with a first label and, as earlier noted particularly for sandwich-type assays, is preferably provided in sufficient quantity to yield a number of reaction sites well in excess of the number of analyte molecules or moieties to be assayed. For a competition assay, the coated cell is contacted with a mixture of the sample that may contain the analyte being assayed and a known quantity of the same analyte tagged with a second label. For the well known sandwich assay, the coated cell would also be contacted with the sample that may contain untagged analyte being assayed, and also with a reagent containing free ligands of that specified type, but tagged with a second label.

For a fluorescent assay, the tags contains fluorophors, in particular compounds such as fluorescein, rhodamine, rare earth chelates and the like. Methods for linking fluorescent tags to a wide variety of analytes, particularly proteinaceous materials, are very well known, and many of the commercially available fluorescent compounds need not be functionalized for attachment because they already have linking groups. For example, a large number of dyes and procedures for coupling same to ligands such as antibodies are described in U.S. Pat. No. 4,166,105 issued Aug. 28, 1979 to Tomas Hirschfeld. Similarly, methods for coupling known luminescent or radioactive tags to analytes are also well known to those skilled in the art and need not be incorporated here.

Signals obtained from the tagged captor ligands immobilized on the substrate and from the immobilized analyte (whether from a tag directly coupled per se to the analyte or from a tagged ligand that secondarily had specifically bound to the analyte depending on the nature of the assay) are then measured. In the ATR system described as exemplary, source 24 is provided for delivering beam 22 of light to cell 10. While source 24 can be a broadband source of light such as a condenser illuminated with light from an incandescent lamp, a light-emitting diode, sunlight and the like, it is preferred that source 24 constitute a dual source to provide excitation radiation within a pair of narrow wavelength bands, and to this end can include appropriate band pass filters. The center wavelengths of the two bands are chosen in accordance with the absorption characteristics of the fluorophors used as the tags on the labeled ligands, so as to excite the latter into fluorescence when illuminated. Light source 24 also includes appropriate beam shaping means, as understood by those skilled in the art, to illuminate objective lens 28 with a beam of appropriate vergence so as to permit lens 28 to image the source aperture on end face 18, preferably with no ray incident on face 18 at an angle greater than that corresponding to the numerical aperture of the fiber.

Means, such as beamsplitter 30, are interposed between source 24 and lens 28. In a preferred embodiment, beamsplitter 30 is formed so as to reflect the two excitation wavelength bands and transmit the respective fluorescent emissions from face 18.

If the sample containing analyte is introduced into interspace 32 between fiber 12 and tube 14, the analyte will react with the immobilized ligand in coating 20 assuming that the ligand has been selected to specifically bind to that analyte and some of the analyte is present in the sample. If now, to perform a sandwich assay, one introduces the second labeled ligand species into interspace 26, the second labeled ligand will also specifically bind both to free analyte and to analyte that had been bound to the immobilized ligand.

Upon introducing a light beam from source 24 at an appropriate angle into face 18 of fiber 12, the beam will propagate through the fiber by total internal reflection, creating an evanescent wave in an evanescent zone (not shown) contiguous with the fiber surface. The evanescent wave, where incident on such bound ligands will cause only those labels or tags disposed within the evanescent zone to fluoresce at two different wavelengths or in two different channels, and a large part of that fluorescence will be directed or tunneled back into the medium of fiber 12, some at or above the critical angle and some below the critical angle. Light directed back into the cell at or above the critical angle will be propagated through fiber 12, some emerging from input face 18.

Measurement of the respective amplitudes of the two different wavelengths of fluorescent light emergent from face 18 by electrooptical detection means 34 will indicate the respective quantitative presence of the bound ligands to which the tags are coupled. To this end means 34 may comprise two electrooptical detectors respectively sensitive to the respective wavelengths. Alternatively, one may also employ, in lieu of source 24 and detection means 34, a fluorimeter having switchable excitation and emission filters respectively appropriate to the excitation and detection of emission from the corresponding tags. Such measurements of the amplitudes of the signals from the tags can then be fed into means 36, such as an appropriately programmed digital computer or a properly hard-wired circuit, to make the desired determination, as described above, of the ratio of analyte to captor. Another alternative is to use a single detector in cases where, as noted above the separation of the signals is done on temporal rather than wavelength terms, and thus the same tag is used for both the immobilized ligand and the second labeled ligand that will be bound to analyte complexed with the immobilized ligand. In such case, the second-occurring signal can be measured at steady state after it has reached equilibrium, or can be monitored dynamically to observe changes in intensity as they occur. As used herein, measuring or monitoring "dynamically" or "ballistically" means and implies measurements of rate of change of the reaction by following the rate of change of the fluorescent signal(s).

A preferred embodiment employs a fluorimeter having switchable excitation and emission filters respectively appropriate to the excitation and detection of fluorescence from two different and distinguishable fluorescent dyes such as fluorescein and rhodamine respectively coupled to the immobilized ligand and to the analyte of interest, i.e., excitation filters 480/20 (480 nm center wavelength, 20 nm band pass) for fluorescein and 530/30 for rhodamine; fluorescence filters of 530/30 for fluorescein and 580/20 for rhodamine.

It will be appreciated that the product of the present invention, at least in the form of an optical fiber ATR cell, can be provided as a disposable, i.e., a product designed for a single use or assay after which it can then be destroyed. Where the antigen being assayed is a particularly pathogenic virus such as Hepatitis B or AIDS, then the use of such a disposable may be desired to provide some protection to the assayer. On the other hand, as noted earlier, single use products may not lend themselves readily to precise duplication and standardization, and their use may also be expensive and time consuming where a large number of assays are to be performed in a relatively short time. Consequently, the present invention is particularly useful for standardizing single-use or disposable products by simply examining the radiation from each to insure that all cells of a predetermined type contain the same amount of ligand within desired limits.

For use of the product of the invention in multiple assays, the solid phase or substrate, typically a fiber, is pre-loaded with immobilized tagged ligand far in excess of the number of antigen molecules that are expected in any individual assay. The fiber is read to determine the strength of the signal from the tag. For a typical sandwich assay, the fiber is then contacted with a first sample and a reagent of free ligands labeled with a tag distinguishable from that coupled to the immobilized ligand. The strength of the signals obtained from the complexed, tagged ligand and the immobilized ligands are then determined. The fiber is subjected to a number of such cycles with successive samples and reagents, each prior sample and reagent being washed out if necessary. Each subsequent measurement of the signals from the tagged immobilized ligand and the complexed tagged reagent ligands, together with a previously determined ratio of the number of complexed tagged reagent ligands bound per solid phase immobilized ligand, will provide information from which one can readily determine the extent of the remaining, uncomplexed immobilized ligand population. Each subsequent sample can thus be assayed on the same fiber until the fiber is saturated or near saturation. The fiber can, if one desires, be then stripped chemically to remove the bound antigen, and reused in additional assays. Alternatively, one can strip the fiber of the coating and all complexes, and recoat it to immobilize a fresh population of tagged ligand. Use of rate of change measurements assists in reusing the same fiber, as the change in signal, rather than the total signal, provides the significant information. Accordingly, even relatively small changes on a large signal are significant and measurable since the large initial signal just becomes a baseline measurement that is eliminated in the calculations.

The utility of the method of the present invention is shown in the following example in which the test chosen was a sandwich assay for whole molecule mouse IgG. The solid phase antibody (goat antimouse IgG from Biomeda Corp Cat. #P68) was labeled with allophycocyanine (APC) and the secondary antibody (goat antimouse IgG from Jackson Immuno Research Cat. #115-025-062) was labeled with tetramethyl rhodamine isothiocyanate (TRITC). The goal of the experiment was to show that under the condition of limiting solid phase antibody (i.e., excess mouse IgG and excess second antibody) the specific signal associated with capture of the second antibody would correlate with the signal from the solid phase antibody. The reagents were prepared as follows:

The stock solution of APC labeled antibody was diluted 10× to a final molar concentration of approximately $3 \times 10^{-6}$. A blocking solution of approximately $1.7 \times 10^{-5}$ molar bovine IgG in normal goat serum (Jackson Immuno Research Cat. #s 001-000-003 and 005-000-121 respectively). A 20× dilution (ca. $5 \times 10^{-7}$ molar) of TRITC-labeled antibody was prepared. All dilutions were made using phosphate buffered saline pH 7.4 (Sigma # 1000-3).

Generally, the APC-labeled antibody was adsorbed onto a quartz fiber, reacted with excess mouse IgG, washed and, reacted with excess TRITC antibody. The fluorescent signals were stimulated and read on two channels. In addition, the nonspecific binding of the second antibody was measured by reacting a fiber onto which no solid phase antibody had been adsorbed.

Specifically, a clean quartz fiber was inserted into the flow cell and placed into the fiber optic fluorimeter. The fiber was washed in flowing phosphate-buffered saline solution (PBS) for three minutes, flow was stopped and the fiber background was measured in both the APC and TRITC channels. APC labeled antibody was then flowed into the chamber with the fiber and allowed to incubate (with no flow) for two minutes. The fiber was again washed in flowing PBS for three minutes. The blocking solution (bovine IgG in normal goat serum) was flowed in and incubated for two minutes followed by a three minute wash. The signal on both channels was again recorded. The fiber was incubated with mouse IgG, washed, then read again. Finally, the fiber was incubated with TRITC labeled antibody, washed, and read again.

This procedure was repeated four times. In the first three repetitions, the same dilution of APC antibody was used (stored in a glass test tube at room temperature between uses). It was noticed that the APC signal monotonically decreased with each trial. It was hypothesized that this decrease was due to adsorption of the APC antibody onto the glass tube surface. In the fourth trial, fresh APC antibody was added to the same tube, thereby increasing the signal level, consistent with the hypothesis. The four measurements used varying dilutions of mouse IgG (from 1:10 to 1:200), but it is believed that even at the lower concentration, mouse IgG was still in excess.

In a separate measurement, the ratio of APC fluorescence to TRITC fluorescence under the condition of equal numbers of antibodies for each label, was measured to be 40. From this ratio, the intensity of the solid phase (APC) signal, and the intensity of the second antibody (TRITC) signal, the ratio of second antibodies bound per solid phase antibody bound can be calculated. Table 1 shows the results. Without knowledge of the solid phase antibody, the c.v. for the measurement is 41%. Use of the solid phase signal reduces this to 14%. Note that the consistency in the ratio confirms the assumption that both mouse IgG and second antibody are in excess.

TABLE 1

| | Solid Phase Signal | Second Antibody Signal* | Ratio** |
|---|---|---|---|
| | 4.391 | .309 | 2.81 |
| | 2.918 | .207 | 2.84 |
| | 1.914 | .100 | 2.09 |
| | 3.191 | .216 | 2.71 |
| avg. | 3.104 | .208 | 2.61 |
| sigma | 1.019 | .086 | 0.35 |
| c.v. | 33% | 41% | 14% |

*NSB has been subtracted
**ratio is the number of second antibodies over the number of solid phase antibodies and is calculated from:

$$\frac{\text{Second Antibody Signal} \times 40}{\text{Solid Phase Signal}}$$

Since certain changes may be made in the above method and apparatus without departing from the scope of the invention involved, it is intended that all matter contained in the above description or shown in the accompanying drawings shall be interpreted as illustrative and not in a limiting sense.

What is claimed is:

1. A method of assaying for an analyte in multiple different fluid samples comprising the steps of:
   a) providing a captor ligand having binding specificity for said analyte, said captor ligand being labeled with a first fluorescent tag;
   b) immobilizing said captor ligand on a portion of the surface of an optical substrate adapted for total internal reflection of optical radiation propagating therethrough;
   c) mixing a known quantity of said analyte labeled with a second fluorescent tag with a fluid sample containing an unknown quantity of unlabeled analyte, said first fluorescent tag and said second fluorescent tag being distinguishable from each other;
   d) contacting said immobilized captor ligand with said mixture of said tagged analyte and said first fluid sample;

e) propagating optical radiation through said optical substrate to produce evanescent wave radiation in an evanescent wave zone adjacent to said surface of said substrate, thereby exciting said first and second fluorescent tags within said evanescent wave zone to produce first and second signals distinguishable from one another within said evanescent wave zone;

f) independently detecting, measuring and comparing said first and said second signal before equilibrium between said analyte and said immobilized captor ligand is reached;

thereby obtaining a measure of the amount of unlabeled analyte in said fluid sample;

g) assaying additional different fluid samples, each containing said analyte, by sequentially repeating steps (c) through (f) on said same portion of the substrate as recited in step (b) with each of said additional samples.

2. The method of claim 1 wherein said captor ligand is an antibody.

3. The method of claim 1 wherein said captor ligand is an antigen.

4. A method for assaying for an analyte in a sample comprising the steps of:

a) providing first and second captor ligands each having binding specificity for said analyte, said first and second captor ligands being labeled, respectively, with first and second fluorescent tags distinguishable from one another;

b) immobilizing said first captor ligand on the surface of an optical substrate adapted for total internal reflection of optical radiation propagating therethrough;

c) contacting said immobilized first captor ligand with a unknown quantity of analyte in said sample to effect specific binding of said analyte to said immobilized first captor ligand;

d) contacting said analyte specifically bound to said immobilized first captor ligand with said second captor ligand to effect specific binding of said second captor ligand to said analyte;

e) propagating optical radiation through said optical substrate to produce evanescent wave radiation in said evanescent wave zone adjacent to said surface of said substrate, thereby exciting said first and second fluorescent tags within said evanescent wave zone to produce first and second signals, respectively;

f) independently detecting, measuring, and comparing said first signals with a rate of change of the intensity of said second signals before equilibrium between said immobilized first captor ligand, said analyte and said second captor ligand is reached, thereby obtaining a measure of the amount of analyte in said sample.

5. The method of claim 4 wherein said first and said second captor ligands are antibodies.

6. The method of claim 4 wherein said first and said second captor ligands are antigens.

7. The method of claim 4 wherein multiple different samples containing the same analyte are assayed on said substrate by sequentially repeating steps (c) though (h) with different samples.

8. A method of assaying for an analyte in a fluid sample, comprising the steps of:

a) providing first and second captor ligands each having binding specificity for said analyte, said first and second captor ligands being labeled, respectively, with first and second fluorescent tags distinguishable from each other;

b) immobilizing said first captor ligand on the surface of an optical substrate adapted for total internal reflection of optical radiation propagating therethrough;

c) introducing said second captor ligand labeled with said second fluorescent tag into said sample containing said analyte, thereby allowing said second ligand and said analyte to form a complex;

d) contacting said immobilized first captor ligand with said sample containing said complex;

e) propagating optical radiation through said optical substrate to produce evanescent wave radiation in an evanescent wave zone adjacent to said surface of said substrate, thereby exciting said first and second fluorescent tags within said evanescent wave zone to produce first and second signals distinguishable from one another within said evanescent wave zone; and f) independently detecting, measuring, and comparing said first signals and the rate of change of the intensity of said second signals before equilibrium between said complex and said immobilized first captor ligand is reached, thereby obtaining a measure of the amount of analyte in said sample.

9. The method of claim 8 wherein said first and said second captor ligands are antibodies.

10. The method of claim 8 wherein said first and said second captor ligands are antigens.

11. The method of claim 8 wherein multiple different samples containing the same analyte are assayed on said substrate by sequentially repeating steps (c) though (f) with different samples.

* * * * *